(12) United States Patent  
Bar-Shalom et al.

(10) Patent No.: US 9,795,745 B2  
(45) Date of Patent: Oct. 24, 2017

(54) SYRINGE WITH A HOLLOW PLUNGER

(71) Applicant: Bioneer A/S, Horsholm (DK)

(72) Inventors: Daniel Bar-Shalom, Kokkedal (DK); Lasse Johansson, Copenhagen (DK)

(73) Assignee: Bioneer A/S, Horsholm (DK)

( * ) Notice: Subject to any disclaimer, the term of this patent is extended or adjusted under 35 U.S.C. 154(b) by 36 days.

(21) Appl. No.: 14/410,777

(22) PCT Filed: Jun. 25, 2013

(86) PCT No.: PCT/EP2013/063199  
§ 371 (c)(1),  
(2) Date: Dec. 23, 2014

(87) PCT Pub. No.: WO2014/001285  
PCT Pub. Date: Jan. 3, 2014

(65) Prior Publication Data  
US 2015/0190584 A1 Jul. 9, 2015

Related U.S. Application Data

(60) Provisional application No. 61/664,184, filed on Jun. 26, 2012, provisional application No. 61/700,381, filed on Sep. 13, 2012.

(30) Foreign Application Priority Data

Sep. 13, 2012 (EP) .................... 12184306

(51) Int. Cl.  
*A61M 37/00* (2006.01)  
*A61M 5/315* (2006.01)  
*F26B 5/06* (2006.01)

(52) U.S. Cl.  
CPC ........... *A61M 5/31596* (2013.01); *F26B 5/06* (2013.01); *A61M 2005/31598* (2013.01); *F04C 2270/0421* (2013.01)

(58) Field of Classification Search  
CPC ...... A61M 5/31596; A61M 2005/1787; A61M 5/16827; A61M 2005/31598  
(Continued)

(56) References Cited

U.S. PATENT DOCUMENTS 3,240,328 A 3/1966 Matteuzzi  
3,269,905 A 8/1966 Damaskus et al.  
(Continued)

FOREIGN PATENT DOCUMENTS

DE 1492621.7 6/1969  
EP 0394050 A2 10/1990  
(Continued)

OTHER PUBLICATIONS

European Examination Report as issued in corresponding European Application No. 13730900.1, dated Oct. 23, 2015.  
(Continued)

*Primary Examiner* — Phillip Gray  
(74) *Attorney, Agent, or Firm* — Alston & Bird LLP

(57) ABSTRACT

A syringe for mixing and ejecting an active pharmaceutical ingredient is disclosed. The syringe is designed in such a manner that it is ensured that substantially all of the mixed drug is ejected, and in such a manner that an active pharmaceutical ingredient can be lyophilized directly into the syringe. The syringe comprises a syringe body, a first plunger arranged movably inside the syringe body and a second plunger arranged movably inside the first plunger. In one aspect the second plunger comprises a first plunger part and a second plunger part, and the first and second plunger parts are adapted to cooperate to collapse the cavity of the first plunger. In a second aspect the cavity of the first plunger has a first diameter at a distal end and a second diameter at a proximal end, the first diameter being smaller than the second diameter.

15 Claims, 9 Drawing Sheets

(58) Field of Classification Search
USPC .................................. 604/89, 90, 191, 218
See application file for complete search history.

(56) References Cited

U.S. PATENT DOCUMENTS

| | | | |
|---|---|---|---|
| 3,616,543 A | 11/1971 | Barclay | |
| 3,718,139 A | 2/1973 | Hanford | |
| 4,351,158 A | 9/1982 | Hurwitz et al. | |
| 4,354,768 A | 10/1982 | Witek | |
| 4,642,102 A * | 2/1987 | Ohmori | A61M 5/31555 604/210 |
| 5,172,807 A * | 12/1992 | Dragan | A61C 5/66 206/219 |
| 5,599,312 A * | 2/1997 | Higashikawa | A61M 5/19 604/191 |
| 5,704,918 A | 1/1998 | Higashikawa | |
| 2011/0089065 A1 | 4/2011 | Bottger et al. | |
| 2012/0259279 A1 | 10/2012 | Finke | |

FOREIGN PATENT DOCUMENTS

| | | |
|---|---|---|
| EP | 0394050 A3 | 10/1990 |
| EP | 2508219 A1 | 10/2012 |
| WO | WO-2004/026377 A1 | 4/2004 |
| WO | WO-2012/104376 A1 | 8/2012 |

OTHER PUBLICATIONS

Extended European Search Report for application EP12184306 dated Feb. 14, 2013.
PCT International Search Report of the International Searching Authority for application PCT/US2013/063199 dated Dec. 2, 2013.

\* cited by examiner

SYRINGE WITH A HOLLOW PLUNGER

CROSS REFERENCE TO RELATED APPLICATION

This application is a national stage application filed under 35 U.S.C. §371 of International Application No. PCT/EP2013/063199 filed Jun. 25, 2013, which claims priority to U.S. Provisional Patent Application No. 61/700,381, filed Sep. 13, 2012, U.S. Provisional Patent Application No. 61/664,184, filed Jun. 26, 2012 and European Patent Office Application 12184306.4, filed Sep. 13, 2012, all of which are hereby incorporated by reference in their entirety.

FIELD OF THE INVENTION

The present invention relates to a syringe for delivering drugs. The syringe of the invention can be used for mixing an active pharmaceutical ingredient in a dry form or in the form of a solution with a liquid diluent, prior to delivery of the mixed drug. The syringe of the invention ensures that essentially all of the mixed drug is delivered from the syringe. The syringe is further suitable for allowing an active pharmaceutical drug to be lyophilized directly into the syringe.

BACKGROUND OF THE INVENTION

Syringes which can be used for mixing an active pharmaceutical ingredient with a liquid diluent, and subsequently delivering the mixed drug are known. One problem with the previous syringes is that the construction allowing the active pharmaceutical ingredient to be mixed with the liquid diluent, creates one or more cavities inside the syringe, where mixed drug is trapped during delivery of the mixed drug. Thereby part of the mixed drug is left inside the syringe, and is therefore not delivered from the syringe.

Another problem with the previous syringes is that, in the case that the active pharmaceutical ingredient is in the form of a lyophilized drug, the lyophilized drug must be prepared separately and subsequently introduced into the syringe. This adds to the manufacturing costs and causes an increased risk of contamination of the drug.

U.S. Pat. No. 5,599,312 discloses a syringe for simultaneous injection of plural medicines, or for injection of solutions of solid medicine. Different kinds of injection agents are accommodated in chamber formed separately in a cylinder, without being previously mixed.

U.S. Pat. No. 4,354,768 discloses a multiple barrel hypodermic syringe for mixing materials contained in the barrels prior to use. The syringe comprises a lower barrel for containing a sterile material such as a lyophilizable product, and an upper barrel containing a liquid diluent.

DESCRIPTION OF THE INVENTION

It is an object of embodiments of the invention to provide a syringe for mixing and ejecting a drug, in which it is ensured that substantially the entire dose of the mixed drug is delivered from the syringe.

It is a further object of embodiments of the invention to provide a syringe which allows an active pharmaceutical ingredient to be easily lyophilized directly into the syringe.

According to a first aspect the present invention provides a syringe comprising
a syringe body,
a first plunger arranged movably inside the syringe body, said first plunger being hollow, thereby defining a cavity,
a second plunger arranged movably inside the cavity of the first plunger, the second plunger comprising a first plunger part and a second plunger part,
wherein a liquid diluent is contained inside the syringe body, and an active pharmaceutical ingredient is contained inside the cavity of the first plunger, separate from the liquid diluent, and wherein the first and/or the second plunger is/are movable in a manner which causes the liquid diluent and the active pharmaceutical ingredient to be mixed, and wherein the first plunger part of the second plunger and the second plunger part of the second plunger are adapted to cooperate to collapse the cavity of the first plunger during operation of the syringe.

It is contemplated that the situation may be reversed, i.e. the active pharmaceutical ingredient may be contained inside the syringe body, and the liquid diluent may be contained inside the cavity of the first plunger, separate from the active pharmaceutical ingredient.

In the present context the term 'syringe' should be interpreted to mean a device which can be used for delivering or ejecting a liquid drug, preferably via a needle attached to or forming part of the syringe.

In the present context the term 'plunger' should be interpreted to mean a part which is movable along a substantially axial direction.

The diluent and the active pharmaceutical ingredient are kept separately from each other. Thereby it is ensured that these do not mix during storage of the syringe. However, the syringe is operable to bring the active pharmaceutical ingredient and the liquid diluent together, thereby mixing them, and to eject or deliver the mixed drug. Thus, the active pharmaceutical ingredient and the diluent can be kept separately during storage, and when it is desired to deliver the drug, the active pharmaceutical ingredient and the diluent can be mixed, using the syringe, and the mixed drug can subsequently be delivered. This will be described in further detail below with reference to the accompanying drawings.

The first plunger part of the second plunger and the second plunger part of the second plunger are adapted to cooperate to collapse the cavity of the first plunger during operation of the syringe. Thereby it is ensured that the cavity of the first plunger is capable of holding the active pharmaceutical ingredient during storage, and of holding a mixed drug during and immediately after the mixing process, while it is ensured that mixed drug contained in the cavity of the first plunger is entirely ejected from the cavity. The cooperation of the first and second plunger parts may take place in a number of ways, as will be described in further detail below.

The syringe may further comprise means for mixing active pharmaceutical ingredient and diluent. The mixing means may, e.g., be in the form of a perforated disk arranged at an end part of the second plunger. The perforated disk can be moved reciprocally inside the syringe body, thereby creating turbulence in the liquid diluent and ensuring that the active pharmaceutical ingredient is properly mixed with the diluent. As an alternative, the syringe could be provided with other devices which can be used for creating turbulence, such as slits or rotating wings.

The first plunger part of the second plunger may be provided with a cavity arranged to receive at least a portion of the second plunger part of the second plunger. According to this embodiment, the second plunger part can be moved into the first plunger part during the mixing and ejection process. Thereby a part of the second plunger is collapsed, thereby causing the cavity of the first plunger, which accommodates the second plunger, to collapse, and ensuring that all of the mixed drug is in fact delivered from the syringe.

As an alternative, the first plunger part of the second plunger and the second plunger part of the second plunger may cooperate in another manner in order to cause the cavity of the first plunger to collapse. For instance, the plunger parts may be provided with alternative mating structures, such as recesses, protruding parts, grooves, tapered sections, etc., allowing the plunger parts to move towards each other in a manner which collapses the cavity of the first plunger.

The second plunger part of the second plunger may be provided with at least one wedge shaped structure on a surface thereof, said wedge shaped structure(s) being adapted to engage with a mating structure provided on a surface of the first plunger part of the second plunger, in such a manner that the first plunger part and the second plunger part are allowed to perform relative movements along one direction, but are prevented from performing relative movements along an opposite direction. Preferably, the first and second plunger parts may be allowed to move relative to each other in a direction which causes the cavity of the first plunger to collapse, but prevented from moving relative to each other in the opposite direction, i.e. in a direction which causes the volume of the cavity of the first plunger to increase. Thus, the wedge shaped structures function as a ratchet.

According to this embodiment, it is possible to assemble the first plunger part and the second plunger part. Once the plunger parts have been assembled, it is not possible to detach them from each other again. Furthermore, it is possible to, e.g., move the second plunger part gradually further towards the first plunger part, while it is not possible to reverse this movement and pull the second plunger part and the first plunger part apart. This prevents that the syringe is accidentally reused.

In the case that the first plunger part of the second plunger has a cavity formed therein, said cavity being arranged to receive a portion of the second plunger part of the second plunger, the wedge shaped structures may advantageously be arranged on an outer part of the second plunger part and inside the cavity of the first plunger part, respectively, in such a manner that the second plunger part can be moved into the cavity of the first plunger part, but is prevented from moving out of the cavity of the first plunger part. Thereby it is possible to move the second plunger part gradually further into the first plunger part, while it is not possible to reverse this movement and pull the second plunger part out of the first plunger part.

As an alternative, the wedge shaped structures may, e.g., be arranged on opposing outer surfaces of the first and second plunger parts.

The second plunger part may be provided with only one wedge shaped structure, or it may be provided with a plurality of wedge shaped structures. In the case that the second plunger part is provided with a plurality of wedge shaped structures, the structures may be provided along the entire length of the second plunger part. Alternatively, they may be provided along a portion of the length of the second plunger part, e.g. at an end of the second plunger part. In this case, some force is required in order to push the first and the second plunger parts into engagement. However, once this has been achieved, the second plunger part can easily be moved further into the first plunger part with little resistance.

The cavity of the first plunger may have a first diameter at a distal end of the first plunger and a second diameter at a proximal end of the first plunger, the first diameter being smaller than the second diameter. A shoulder may be formed between the two regions, e.g. in the form of a tapered section or in the form of a wall part arranged substantially perpendicularly to an axial direction of the syringe.

In the present context the term 'distal end' should be interpreted to mean a part of the syringe where the mixed drug is ejected, and the term 'proximal end' should be interpreted to mean a part of the syringe which is arranged opposite to the distal end, along an axial direction of the syringe.

According to this embodiment the cross sectional area of the cavity of the first plunger is smaller at the distal end than at the proximal end. Thereby a passage may be formed between the inner wall of the cavity of the first plunger and a part of the second plunger, at the distal end, while it is possible for this part of the second plunger to seal the distal end of the cavity of the first plunger when it is moved into the region with the smaller diameter. This makes the syringe suitable for allowing an active pharmaceutical ingredient to be lyophilized directly into the syringe for the following reasons. A substance containing the active pharmaceutical ingredient may be arranged in the cavity of the first plunger, at the distal end, i.e. in the region of the small diameter of the cavity. A part of the second plunger is then arranged in the proximal region of the cavity of the first plunger, i.e. in the region of the larger diameter. The syringe, or at least the first plunger with the substance and the second plunger arranged therein, is then arranged in standard lyophilisation equipment, and a standard lyophilisation process is performed. As described above, a passage is formed between the second plunger and the inner wall of the cavity of the first plunger, and gas and moisture is therefore allowed to escape via this passage during lyophilisation. When the lyophilisation process has been completed, the second plunger is pushed in a distal direction, using standard equipment, thereby moving the second plunger into the region of the small diameter of the cavity of the first plunger. Thereby the distal region, containing the lyophilized drug, is sealed by means of the second plunger, while the syringe is still arranged in the lyophilisation apparatus.

It is an advantage that the process described above can be performed using standard lyophilisation equipment, because no customized equipment is thereby required, and thereby the manufacturing costs can be minimised. Furthermore, the risk of contamination of the active pharmaceutical ingredient is minimised.

The first diameter may be selected in such a manner that a tight fit is provided between an inner surface of the cavity of the first plunger and an outer surface of the second plunger in the region of the first diameter. Thereby the second plunger can be used for sealing the cavity of the first plunger, as described above.

The second diameter may further be selected in such a manner that the cavity of the first plunger can be evacuated via a passage between the second plunger and the first plunger, when the second plunger is arranged in a region corresponding to the second diameter, as described above.

The active pharmaceutical ingredient may be in the form of a lyophilized drug. Alternatively, the active pharmaceutical ingredient may be in any other suitable dry or liquid form.

The active pharmaceutical ingredient may be lyophilized directly into the cavity of the first plunger, and the second plunger may seal the cavity of the first plunger. According to this embodiment, the first plunger, including the active pharmaceutical ingredient, may be positioned inside normal lyophilisation equipment, and lyophilisation may then take place. During this, the second plunger may be arranged inside the first plunger in a region corresponding to the second diameter as described above. Thereby the cavity of the first plunger can be evacuated during the lyophilisation process. When the lyophilisation is completed, the second plunger is pushed further into the first plunger, thereby entering a region corresponding to the first diameter. Thereby a tight fit between the first plunger and the second plunger is provided, and the cavity of the first plunger is sealed.

The active pharmaceutical ingredient may be lyophilized directly onto a surface of the second plunger part of the second plunger, the second plunger part of the second plunger being arranged inside the cavity of the first plunger, and the first plunger part of the second plunger may seal the cavity of the first plunger. According to this embodiment, the first plunger part of the second plunger and the second plunger part of the second plunger may be separated from each other during the lyophilisation process. When the lyophilisation process has been completed, the plunger parts may be assembled, while the first plunger part is moved into a sealing position.

The active pharmaceutical ingredient may be in the form of a lyophilized composition comprising two or more substances. In this case, the active pharmaceutical ingredient may form a layered structure. This may, e.g., be obtained using the following process.

A lyophilized, or freeze-dried, composition comprising two or more substances may be produced in a single container using a method comprising the steps:
i) Providing a first solution comprising at least one first substance in a first solvent in the container;
ii) Cooling said container comprising the first solution to a temperature in the range −150° C. to the freezing point of the first solution;
iii) Adding a second solution comprising at least one second substance in a second solvent at a temperature in the range from a supercooled state to 10° C. above the freezing-point of the second solution to the container obtained in step ii);
iv) cooling to a temperature in the range −150° C. to the freezing point of the second solution;
v) Optionally repeating steps iii) and iv) for each further substance;
vi) Freeze-drying, or lyophilizing, in a manner known per se.

The method may further comprise after step ii) and before step iii) a step of adding a separating layer to a top of the first substance layer at a temperature in the range from minus 70° C. to minus 40° C., such as minus 60° C. to minus 50° C. Thus in order to further prevent interaction between two or more substances a physical barrier may be provided between each substance layer.

According to a second aspect the invention provides a syringe comprising
a syringe body,
a first plunger arranged movably inside the syringe body, said first plunger being hollow, thereby defining a cavity, said cavity having a first diameter at a distal end of the first plunger and a second diameter at a proximal end of the first plunger, the first diameter being smaller than the second diameter,
a second plunger arranged movably inside the cavity of the first plunger,
wherein a liquid diluent is contained inside the syringe body, and an active pharmaceutical ingredient is contained inside the cavity of the first plunger, separate from the liquid diluent, and wherein the first and/or the second plunger is/are movable in a manner which causes the liquid diluent and the active pharmaceutical ingredient to be mixed.

It should be noted that a person skilled in the art would readily recognise that any features described in combination with the first aspect of the invention could also be combined with the second aspect of the invention, and vice versa. The remarks set forth above are therefore equally applicable here.

In the syringe according to the second aspect of the invention the cavity of the first plunger has a diameter which varies along an axial direction of the syringe in such a manner that the diameter is smaller at the distal end than at the proximal end. As described above, this allows an active pharmaceutical ingredient to be lyophilized directly into the cavity of the first plunger, while allowing the cavity to be subsequently sealed by the second plunger, preferably while the syringe is still arranged in the lyophilisation equipment.

Thus, the second diameter may be selected in such a manner that a tight fit is provided between an inner surface of the cavity of the first plunger and an outer surface of the second plunger in the region of the first diameter.

The second plunger may comprise a first plunger part having an outer diameter which matches the first diameter of the first cavity, and a second plunger part having an outer diameter, which is smaller than the outer diameter of the first plunger part, and the second plunger part may be arranged in the cavity of the first plunger in the region of the first diameter. Since the diameter of the second plunger part of the second plunger is smaller than the diameter of the first plunger part of the second plunger, and since the diameter of the first plunger part has a diameter which matches the first diameter of the cavity of the first plunger, there will be a distance between the inner surface of the cavity of the first plunger and the outer surface of the second plunger part of the second plunger. This distance provides space for accommodating the active pharmaceutical ingredient in the first cavity. Furthermore, the first plunger part of the second plunger can be moved into the region of the first diameter of the cavity of the first plunger, thereby sealing the part of the cavity which contains the active pharmaceutical ingredient.

The first plunger part of the second plunger may be provided with one or more protruding parts arranged to abut a portion of an inner wall of the cavity of the first plunger. The portion of the inner wall of the cavity may, e.g., be or form part of a transition region between the region having a small diameter and the region having a larger diameter. The protruding parts allow the first plunger part of the second plunger to be arranged inside the cavity of the first plunger in such a manner that one or more passages are formed between the inner wall of the cavity and the first plunger part of the second plunger. Thereby gas and/or moisture is allowed to escape from the cavity during a lyophilisation process, even though the first plunger part of the second plunger is arranged inside the cavity. The protruding parts are preferably sufficiently resilient to allow the first part of the second plunger to be pushed into sealing engagement with the inner wall of the cavity of the first plunger. Thus, according to this embodiment, the active pharmaceutical ingredient can readily be lyophilized directly into the cavity of the first plunger, and the cavity can subsequently be sealed by means of the first plunger part of the second plunger, without having to remove the syringe from the lyophilisation equipment.

The cavity of the first plunger may comprise a transition region between the region having the first diameter and the region having the second diameter, said transition region defining a shoulder arranged to abut an outer surface of the second plunger. The shoulder may, e.g., be a tapered shoulder. Alternatively, the shoulder may be arranged substantially perpendicularly to an axial direction of the syringe. According to this embodiment, the second plunger may rest loosely against the shoulder in such a manner that gas and/or moisture is allowed to pass, as described above. Subsequently, the second plunger may be pushed past the shoulder and into sealing engagement with the inner wall of the cavity.

The transition region may be provided with one or more protruding parts. Similarly to the embodiment described above, such protruding parts may ensure that one or more passages are formed between the transition region and the second plunger, thereby allowing gas and/or moisture to escape from the cavity during a lyophilisation process.

As an alternative, a passage between the second plunger and the inner wall of the first plunger may be ensured in other ways. For instance, the second plunger part of the second plunger may be arranged inside the cavity of the first plunger in such a manner that it extends beyond a transition region of the cavity. Thereby the first plunger part of the second plunger may rest against the second plunger part during lyophilisation, leaving a gap between the first plunger part and the inner wall of the cavity of the first plunger. When the lyophilisation process has been completed, the first plunger part may be pushed towards the second plunger part, e.g. allowing a part of the second plunger part to enter a cavity of the first plunger part, thereby providing sealing of the cavity of the first plunger by means of the first plunger part of the second plunger.

BRIEF DESCRIPTION OF THE DRAWINGS

The invention will now be described in further detail with reference to the accompanying drawings in which.

DETAILED DESCRIPTION OF THE DRAWINGS

Figure 1:
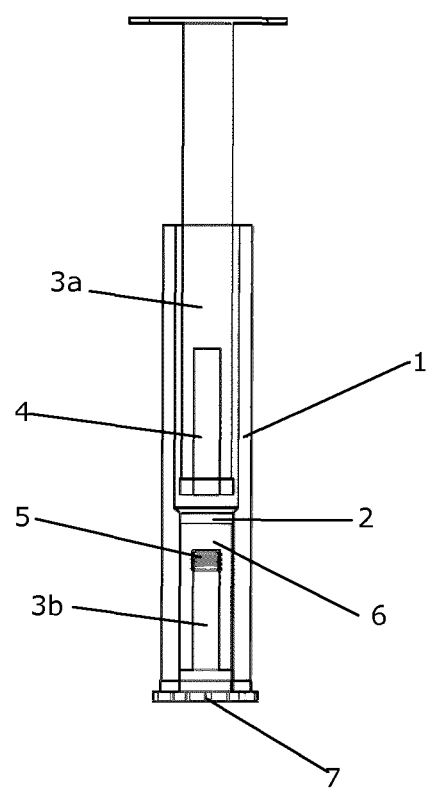
FIGS. 1-4 are cross sectional views of a first plunger and a second plunger of a syringe according to an embodiment of the invention, in various mutual positions.

FIG. 1 is a cross sectional view of a first plunger 1 for a syringe according to an embodiment of the invention. The first plunger 1 is hollow, thereby defining a cavity 2 inside the first plunger 1. A second plunger 3, comprising a first plunger part 3a and a second plunger part 3b, is arranged movably inside the cavity 2. In FIG. 1 the first plunger part 3a and the second plunger part 3b have not yet been assembled to form the second plunger 3, i.e. they are detached from each other.

The cavity 2 has a first diameter in a distal region and a second diameter in a proximal region, the first diameter being smaller than the second diameter. In FIG. 1 the first plunger part 3a is arranged in the proximal region and the second plunger part 3b is arranged in the distal region.

The first plunger part 3a is provided with a cavity 4 adapted to receive the second plunger part 3b. This will be described in further detail below.

The second plunger part 3b is provided with a plurality of wedge shaped structures 5 arranged to engage with mating parts of the cavity 4 of the first plunger part 3a when the second plunger part 3b is moved into the cavity 4. This will be described in further detail below.

An active pharmaceutical ingredient 6 is contained inside the cavity 2 of the first plunger 1.

A perforated disk 7 is mounted at an end part of the second plunger part 3b of the second plunger 3.

Figure 2:
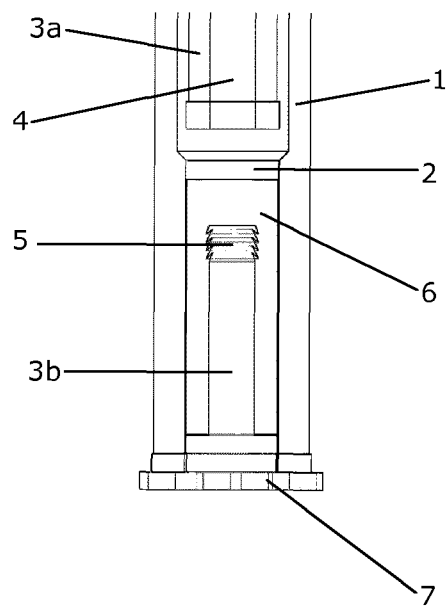

FIG. 2 is a detail of FIG. 1. It can be seen that a relatively large amount of active pharmaceutical ingredient 6 is present in the cavity 2 of the first plunger 1. The active pharmaceutical ingredient 6 is in a liquid form, and is about to be lyophilized. Accordingly, the first plunger 1, including the active pharmaceutical ingredient 6, the first plunger part 3a and the second plunger part 3b, is positioned inside normal lyophilisation equipment.

Figure 3:
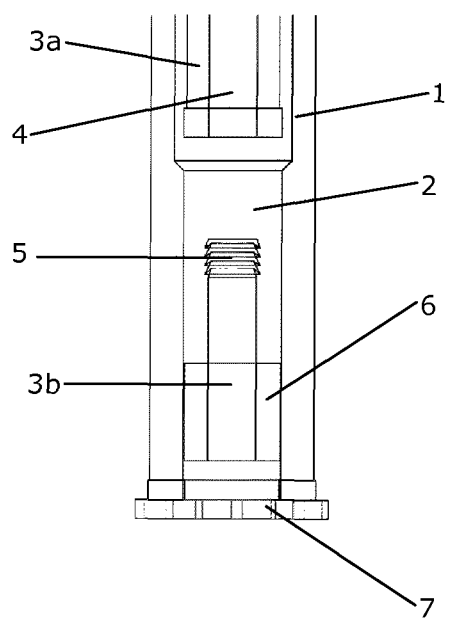

FIG. 3 shows the plungers 1, 3 of FIGS. 2 and 3, after lyophilisation has taken place. It is clear that the amount of active pharmaceutical ingredient 6 has been reduced, as compared to the situation illustrated in FIG. 2. The first plunger part 3a is still arranged in the proximal, high diameter, end of the cavity 2 of the first plunger 1. This allows venting of the cavity 2 of the first plunger 1 during the lyophilisation process, along the first plunger part 3a.

Figure 4:
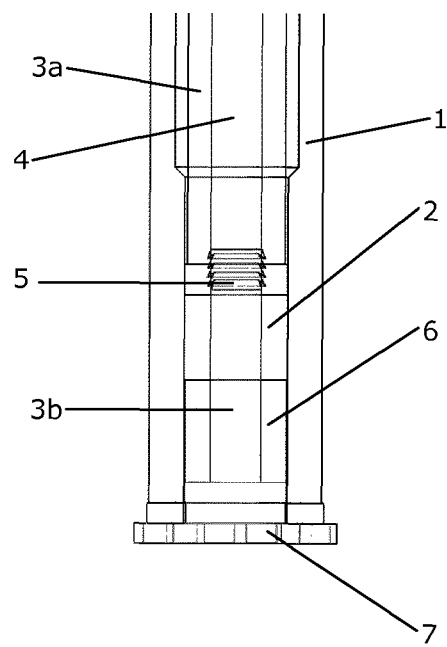

In FIG. 4 the first plunger part 3a has been moved towards the distal end of the first plunger 1. Thereby a part of the wedge shaped structures 5 has been moved into the cavity 4 of the first plunger part 3a, thereby locking the first plunger part 3a and the second plunger part 3b together. Furthermore, the first plunger part 3a has been moved into the part of the cavity 2 of the first plunger 1, which has a smaller diameter. Thereby a tight fit is provided between the first plunger 1 and the second plunger 3, and the second plunger 3 thereby provides sealing for the cavity 2 of the first plunger 1.

Figure 5:
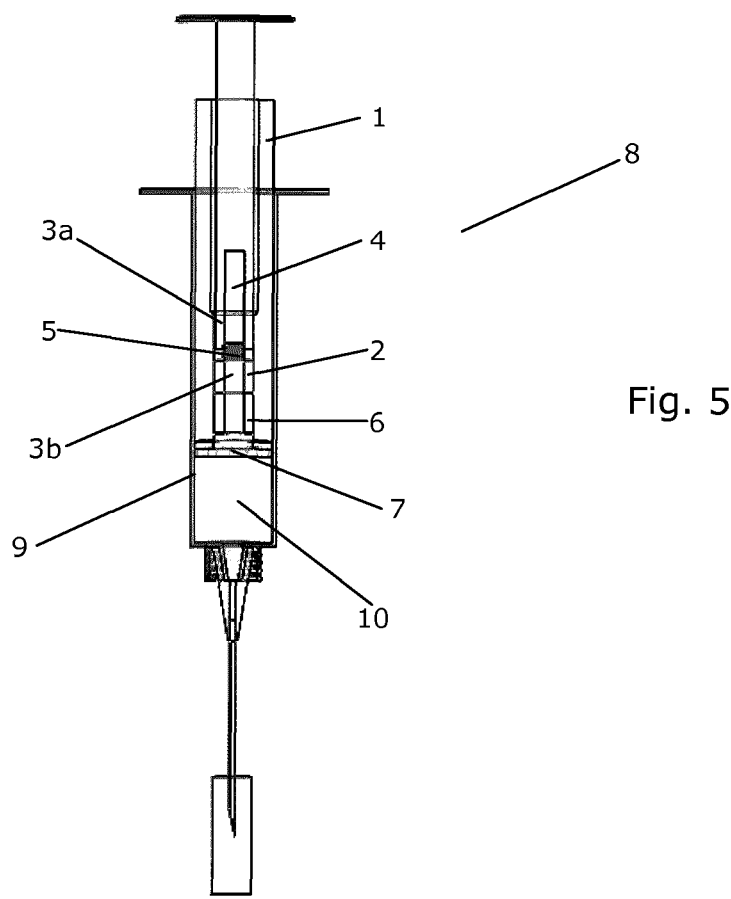
FIGS. 5-8 are cross sectional views of a syringe according to an embodiment of the invention during various stages of a mixing and ejection process.

FIG. 5 is a cross section view of a syringe 8 according to an embodiment of the invention. The syringe 8 of FIG. 5 comprises a syringe body 9, and the plungers 1, 3 of FIGS. 1-4 are arranged movably inside the syringe body 9. A liquid diluent 10 is further contained inside the syringe body 9. FIG. 5 shows the syringe 8 during storage, i.e. the active pharmaceutical ingredient 6 and the liquid diluent 10 are kept separate from each other.

Figure 6:
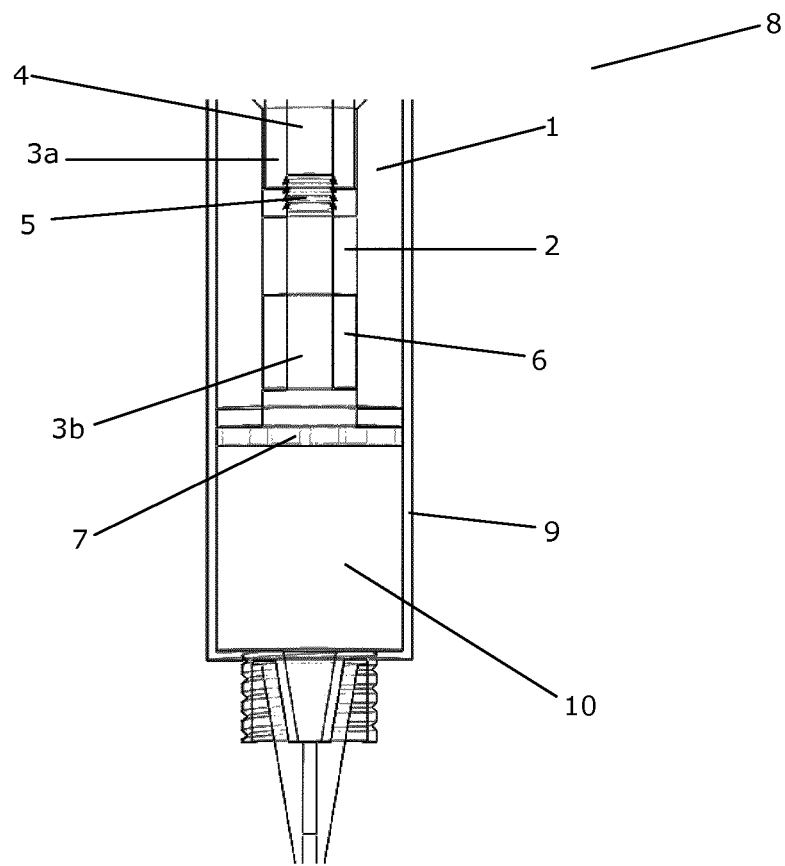

FIG. 6 shows a detail of FIG. 5.

Figure 7:
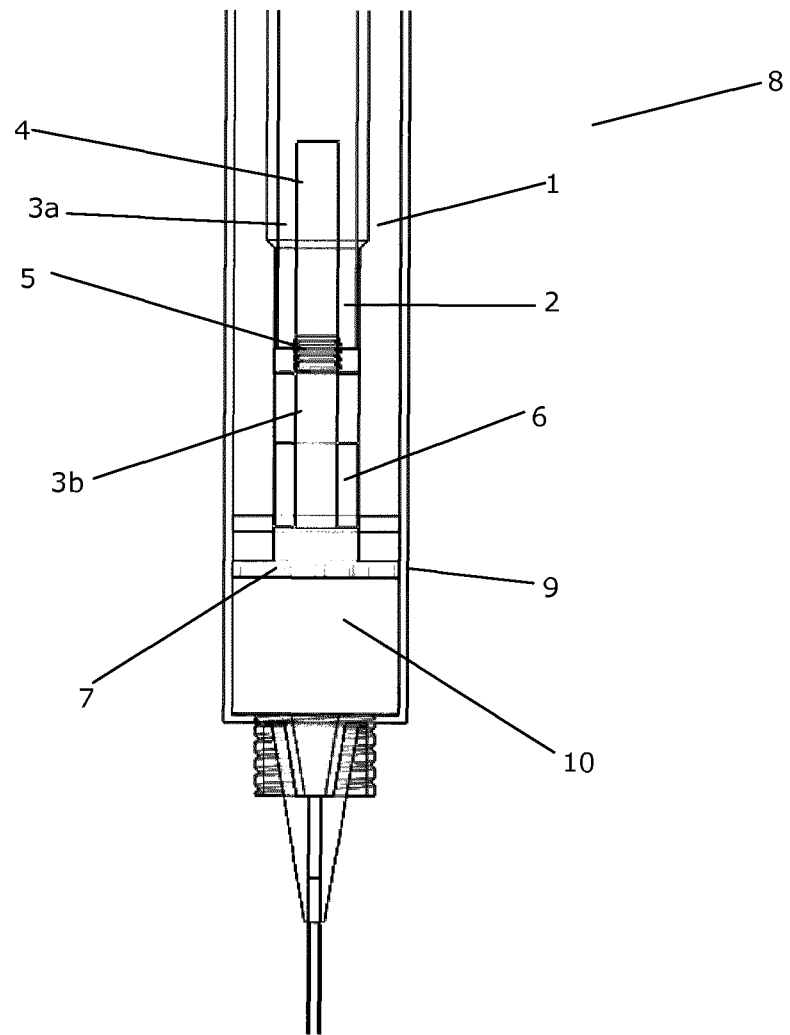

FIG. 7 shows the syringe 8 of FIGS. 5 and 6. In FIG. 7 the second plunger 3 has been moved slightly in a distal direction, thereby bringing the active pharmaceutical ingredient 6 into the region containing the liquid diluent 10, in order to mix the two. The second plunger 3 is then moved reciprocally. Thereby the perforated disk 7 causes turbulence in the liquid diluent 10, thereby ensuring proper mixing of the active pharmaceutical ingredient 6 and the liquid diluent 10.

Figure 8:
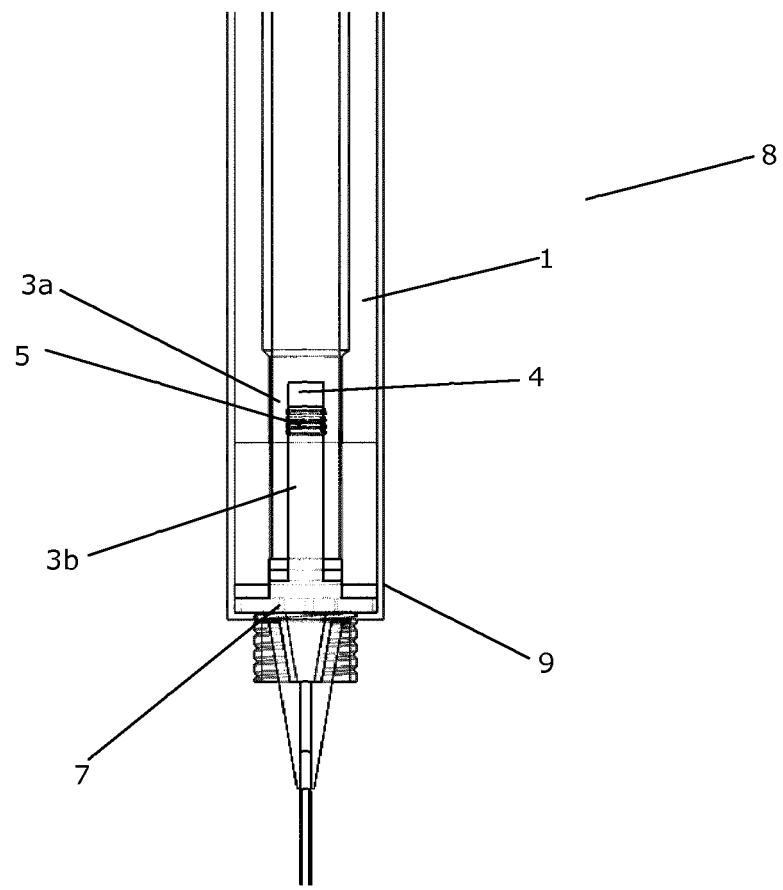

In FIG. 8 the first plunger 1 has been moved as far as possible in the distal direction. Furthermore, the first plunger part 3a of the second plunger 3 has been moved in a distal direction. As a result of this, the second plunger part 3b has been moved completely into the cavity 4 of the first plunger part 3a, thereby collapsing a part of the second plunger 3. The movements of the first plunger 1 and the second plunger 3 have caused the mixed drug to be ejected from the syringe 8. Since the second plunger part 3a has been moved into the cavity 4 of the first plunger part 3a, the cavity 2 of the first plunger 1 has collapsed, and it has been possible to eject essentially all of the mixed drug from the syringe 8. Thus, a reliable dose of drug has been delivered, and a minimal waste has been obtained.

Figure 9:
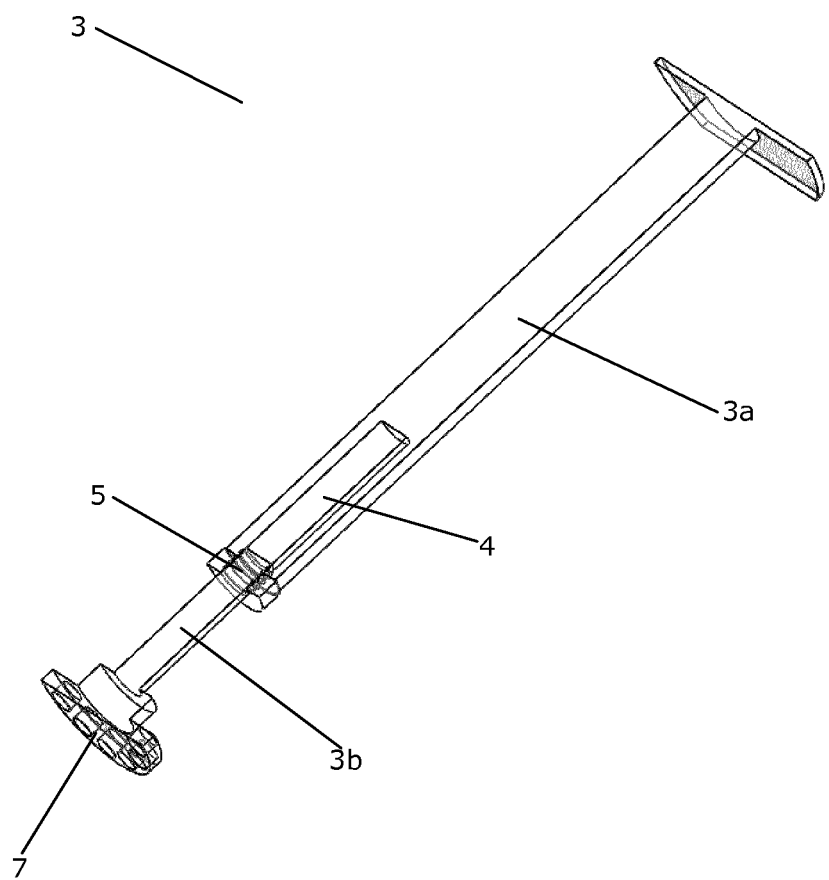
FIG. 9 is a perspective view of a second plunger for a syringe according to an embodiment of the invention, with a part of the plunger broken away.

FIG. 9 is a perspective view of a second plunger 3 for a syringe according to an embodiment of the invention. A part of the plunger 3 has been broken away for clarity. It is clear from FIG. 9 how the second plunger part 3b is received in the cavity 4 of the first plunger part 3a, and how the wedge shaped parts 5 engage with an inner surface of the cavity 4. It is also clear that the second plunger part 3b can be moved further into the cavity 4.

Figure 10:
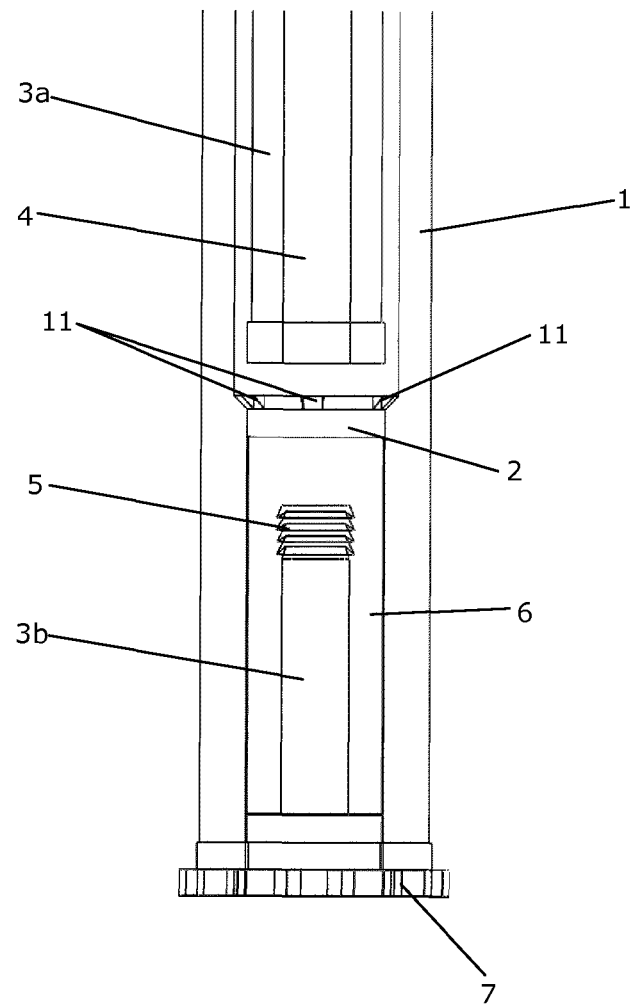
FIG. 10 is a cross sectional view of a first plunger and a second plunger of a syringe according to an alternative embodiment of the invention.

FIG. 10 is a cross sectional view of a first plunger 1 and a second plunger 3 for a syringe according to an alternative embodiment of the invention. The plungers 1, 3 of FIG. 10 are very similar to the plungers 1, 3 shown in FIGS. 1-4, and they will therefore not be described in detail here.

Similarly to the situation described above with reference to FIGS. 1-4, the first plunger 1 of FIG. 10 defines a cavity 2 having a first diameter in a distal region and a second diameter in a proximal region, the first diameter being smaller than the second diameter. The transition region between the distal region and the proximal region of the cavity 2 is provided with a number of protruding parts 11, three of which are visible.

When the first plunger part 3a of the second plunger is arranged in the proximal region, during lyophilisation of the active pharmaceutical ingredient 6, the first plunger part 3a rests against the protruding parts 11. Thereby it is ensured that the first plunger part 3a of the second plunger remains in the proximal region, and that venting of the cavity 2 can take place via passages formed between the protruding parts 11 during lyophilisation of the active pharmaceutical ingredient 6. However, once the lyophilisation has been completed, it is possible to push the first plunger part 3a past the protruding parts 11 and into the distal region of the cavity 2, thereby sealing the cavity, as described above.

It should be noted that, even though the protruding parts 11 are formed on a wall part of the transition region between the proximal region and the distal region of the cavity 2, in the embodiment of FIG. 10, the skilled person would readily recognise that a similar effect can be obtained by providing an end part of the first plunger part 3a with similar protrusions.

Figure 11:
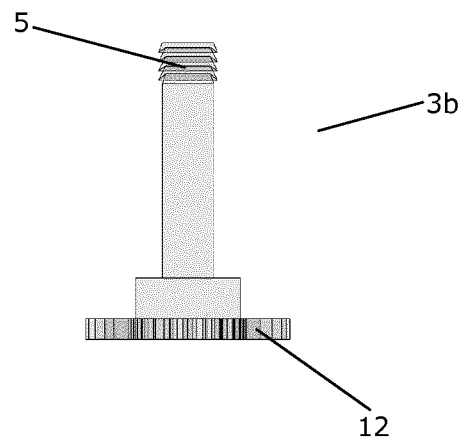
FIGS. 11 and 12 show a second plunger part of a second plunger of a syringe according to another alternative embodiment of the invention.

FIG. 11 is a side view of a second plunger part 3b of a second plunger of a syringe according to another alternative embodiment of the invention. The second plunger part 3b has a mixing element 12 mounted at an end part thereof. The mixing element 12 replaces the perforated disk 7 shown in FIGS. 2-4 and described above. The mixing element 12 will be described in further detail below with reference to FIG. 12.

Figure 12:
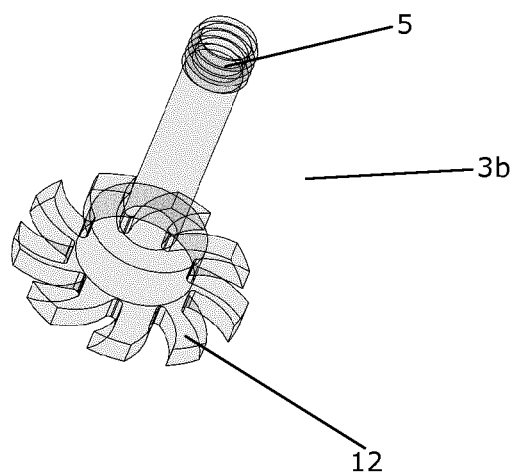

FIG. 12 is a perspective view of the second plunger part 3b of FIG. 11. In FIG. 12 the mixing element 12 is clearly visible, and it can be seen that the mixing element 12 comprises a plurality of spaced apart mixing arms. During mixing of the active pharmaceutical ingredient and the diluent, the mixing element 12 may be moved reciprocally, as described above with respect to the perforated disk 7, in order to cause turbulence on the liquid diluent, thereby ensuring proper mixing of the active pharmaceutical ingredient and the liquid diluent. As an alternative, the mixing element 12 may be rotated about an axis defined by the second plunger 3. In this case rotation of the mixing arms will cause the required turbulence of the liquid diluent, thereby ensuring proper mixing of the active pharmaceutical ingredient and the liquid diluent.

The invention claimed is:

1. A syringe comprising
a syringe body,
a first plunger arranged movably inside the syringe body, said first plunger being hollow, thereby defining a cavity,
a second plunger arranged movably inside the cavity of the first plunger, the second plunger comprising a first plunger part and a second plunger part,
wherein a liquid diluent is contained inside the syringe body, and an active pharmaceutical ingredient is contained at a distal end inside the cavity of the first plunger, separate from the liquid diluent, wherein the first and/or the second plunger is/are movable in a manner which causes the liquid diluent and the active pharmaceutical ingredient to be mixed, and wherein the first plunger part of the second plunger and the second plunger part of the second plunger are adapted to cooperate to collapse the cavity of the first plunger during operation of the syringe, and,
wherein the cavity of the first plunger has a first diameter at a distal end of the first plunger and a second diameter at a proximal end of the first plunger, the first diameter being smaller than the second diameter, a transition region between the proximal end and the distal end being provided with a number of protruding parts, thereby forming a passage between an inner wall of the cavity of the first plunger and a part of the second plunger, at the distal end, when the second plunger rests against the protruding parts, this part of the second plunger being configured to seal the distal end of the cavity of the first plunger when it is moved past the protruding parts and into a region with the first diameter.

2. A syringe according to claim 1, further comprising means for mixing active pharmaceutical ingredient and diluent.

3. A syringe according to claim 1, wherein the first plunger part of the second plunger has a cavity formed therein, said cavity being arranged to receive at least a portion of the second plunger part of the second plunger.

4. A syringe according to claim 1, wherein the second plunger part of the second plunger is provided with at least one wedge shaped structure on a surface thereof, said wedge shaped structure(s) being adapted to engage with a mating structure provided on a surface of the first plunger part of the second plunger, in such a manner that the first plunger part and the second plunger part are allowed to perform relative movements along one direction, but are prevented from performing relative movements along an opposite direction.

5. A syringe according to claim 1, wherein the first diameter is selected in such a manner that a tight fit is provided between an inner surface of the cavity of the first plunger and an outer surface of the second plunger in the region of the first diameter.

6. A syringe according to claim 1, wherein the active pharmaceutical ingredient is in the form of a lyophilized drug.

7. A syringe according to claim 6, wherein the active pharmaceutical ingredient is lyophilized directly into the cavity of the first plunger, and wherein the second plunger seals the cavity of the first plunger.

8. A syringe according to claim 7, wherein the active pharmaceutical ingredient is lyophilized directly onto a surface of the second plunger part of the second plunger, the second plunger part of the second plunger being arranged inside the cavity of the first plunger, and wherein the first plunger part of the second plunger seals the cavity of the first plunger.

9. A syringe according to claim 6, wherein the active pharmaceutical ingredient is in the form of a lyophilized composition comprising two or more substances.

10. A syringe according to claim 9, wherein the active pharmaceutical ingredient forms a layered structure.

11. A syringe comprising
a syringe body,
a first plunger arranged movably inside the syringe body, said first plunger being hollow, thereby defining a cavity, said cavity having a first diameter at a distal end of the first plunger and a second diameter at a proximal end of the first plunger, the first diameter being smaller than the second diameter, and a transition region between the proximal end and the distal end being provided with a number of protruding parts,
a second plunger arranged movably inside the cavity of the first plunger, thereby forming a passage between an inner wall of the cavity of the first plunger at a part of the second plunger, at the distal end, when the second plunger rests against the protruding parts, this part of the second plunger being configured to seal the distal end of the cavity of the first plunger when it is moved past the protruding parts and into a region with the first diameter,
wherein a liquid diluent is contained at the distal end inside the syringe body, and an active pharmaceutical ingredient is contained inside the cavity of the first plunger, separate from the liquid diluent, and wherein the first and/or the second plunger is/are movable in a manner which causes the liquid diluent and the active pharmaceutical ingredient to be mixed.

12. A syringe according to claim 11, wherein the second diameter is selected in such a manner that a tight fit is provided between an inner surface of the cavity of the first plunger and an outer surface of the second plunger in the region of the first diameter.

13. A syringe according to claim 11, wherein the second plunger comprises a first plunger part having an outer diameter which matches the first diameter of the first cavity, and a second plunger part having an outer diameter, which is smaller than the outer diameter of the first plunger part, wherein the second plunger part is arranged in the cavity of the first plunger in the region of the first diameter.

14. A syringe according to claim 13, wherein the first plunger part of the second plunger is provided with one or more protruding parts arranged to abut a portion of an inner wall of the cavity of the first plunger.

15. A syringe according to claim 11, wherein the cavity of the first plunger comprises a transition region between the region having the first diameter and the region having the second diameter, said transition region defining a shoulder arranged to abut an outer surface of the second plunger.

* * * * *